United States Patent [19]

Laptewicz, Jr. et al.

[11] Patent Number: 4,611,588

[45] Date of Patent: Sep. 16, 1986

[54] LASER BEAM RESISTANT MATERIAL

[75] Inventors: Joseph E. Laptewicz, Jr., Groton; Roland Bauer, Mystic, both of Conn.

[73] Assignee: Pfizer Hospital Products Group, Inc., New York, N.Y.

[21] Appl. No.: 741,336

[22] Filed: Jun. 5, 1985

[51] Int. Cl.$^4$ .............................................. A61F 13/00
[52] U.S. Cl. ........................... 128/132 R; 128/207.14; 128/207.15; 252/511; 523/136
[58] Field of Search ...................... 128/207.14, 207.15, 128/132 R; 252/511; 523/136

[56] References Cited

U.S. PATENT DOCUMENTS

| | | | |
|---|---|---|---|
| 3,512,183 | 5/1970 | Sharp et al. | 252/511 X |
| 3,742,423 | 6/1973 | Chadwick | 252/511 X |
| 3,849,345 | 11/1974 | Snavely | 252/511 |
| 3,861,029 | 1/1975 | Smith-Johannsen et al. | 252/511 X |
| 3,862,056 | 1/1975 | Hartman | 252/511 |
| 4,377,164 | 3/1983 | Sabbota | 128/207.14 |
| 4,489,722 | 12/1984 | Ferraro et al. | 128/207.15 |

*Primary Examiner*—Lucille M. Phynes
*Attorney, Agent, or Firm*—Charles J. Knuth; Peter C. Richardson; Harold W. Ordway

[57] ABSTRACT

A shielding material for use in such as endotracheal tubes during laser beam surgery comprising a dispersion of particulate graphite in a polymer matrix.

10 Claims, No Drawings

LASER BEAM RESISTANT MATERIAL

BACKGROUND OF THE INVENTION

This invention concerns a shielding material for use in such as laser beam surgery.

Laser technology is playing an increasingly important role in today's surgical procedures, as illustrated by its use in throat surgery. Such use, however, does present certain problems. For example, the laser beam can severely damage the endotracheal tube commonly used during throat operations, an accidental direct burst from the laser having the capability of burning through the unprotected wall of the tube and thereby destroying its function.

To avoid such burning, the tube may be wrapped with reflective aluminum tape. While this wrapping does prevent destruction of the tube itself, the reflected beam may well cause thermal damage elsewhere. In addition, the heavy aluminum tape traumatizes the patient's throat. A similar approach to the problem is described in U.S. Pat. No. 4,489,722, in which the tube is provided with a dip-coated laser-reflective coating. While this is an improvement over the aluminum wrapping, the coating makes the tube much less flexible, and laser blasts are still reflected from the tube into the throat tissue.

The need therefore exists for a more effective means of protecting endotracheal tubes and other medical devices employed with laser beam surgery.

SUMMARY OF THE INVENTION

It has now been found that the incorporation of graphite particles into a polymeric matrix can produce a suitably flexible composite material capable of receiving direct laser beam impingement with a minimum of both thermal destruction to the material and reflection of the beam to surrounding tissue.

The present invention therefore entails a a shield for protecting matter from laser beam impingement, the shield being fabricated from a composite comprising a dispersion of particulate graphite in a polymer matrix.

Preferably, the particulate graphite is pyrolytic graphite, is at least partially oriented in the polymer matrix, constitutes from about 25 to 35 weight percent of the composite and has an average particle size of from about 50 to 100 microns when used with such as carbon dioxide lasers, while the polymer matrix is silicone rubber. The shield is preferably in the form of a sheet or tube, particularly as an endotracheal tube fabricated from a composite comprising a dispersion of particulate pyrolytic graphite in an elastomer matrix.

The present invention also entails a method of reducing the effects from laser beam impingement on a heat-sensitive implement or living tissue, such as during laser beam surgery, which comprises protecting the implement or tissue with a layer of composite material comprising a dispersion of particulate graphite in a polymer matrix, the particulate graphite preferably being pyrolytic graphite at least partially oriented in the polymer matrix.

DETAILED DESCRIPTION OF THE INVENTION

When a laser beam, or coherent amplified light, strikes the surface of matter, considerable heat energy may be transferred from the beam to the matter. To be compatible in laser beam surgery, a material should be capable of absorbing the incident beam energy and rapidly dissipating the resultant heat energy from the immediate area of the laser impact. The composite material of the present invention, in which particulate graphite is dispersed in a polymer matrix to take advantage of graphite's unique anisotropic properties, has shown considerable ability to absorb and dissipate laser beam energy and thus protect both the material itself and its surroundings from the detrimental effects of accidental laser beam impingement.

The particulate graphite used for the dispersion may be any predominately (greater than 50 percent) graphitic carbon. Graphitic carbon is a form of elemental carbon with a 3-dimensional ordering, consisting of flat, parallel (a-b) planes of carbon atoms, the atoms within each plane forming an ordered hexagonal pattern of condensed planar $C_6$ rings, the planes being spaced 3.354 A° apart and the individual crystals, or crystallites, exceeding 200 A° in diameter. With such an ordering, the bonding force between the planes is only about 2 percent of that within a plane, resulting in a marked anisotropy of most properties, including heat conduction. Natural graphite, depending upon its source, may be from about 85 to 100 percent graphitic carbon, while synthetic graphite, produced by heating either amorphous carbon or a baked petroleum coke product above 2200° C., is normally about 85 percent graphitic.

A particularly suitable graphite for use in the practice of the present invention is pyrolytic graphite. Pyrolytic graphite is an essentially pure graphite formed by a vapor phase deposition process in which a hydrocarbon gas is pyrolyzed in a high temperature vacuum furnace and the resulting carbon deposited on a planar surface with the basal planes of the deposited carbon oriented parallel to this surface. Within each basal plane, or turbostratic layer, the carbon atoms are arranged in 2-dimensional hexagons with each atom strongly bonded to three other atoms. Between the planes, however, the bonding is achieved primarily by Van der Waal forces. This great difference in bonding strength accounts for the extreme directionality, or anisotropy, of pyrolytic graphite: Parallel to the deposition surface, or a-b plane, the pyrolytic graphite has a thermal conductivity equivalent to metals, while perpendicular to this plane, it has a thermal insulation property similar to that of ceramics. This difference in thermal conductivity is about 200 to 1.

It is this anisotropy of graphite, along with its inert and refractory nature, which makes it so effective in protecting such as an endotracheal tube from stray laser beam impingement of its surface, the absorbed heat from a hit being quickly dissipated in all directions throughout the tube. Further, by selecting the proper size for the graphite particles, as explained hereinbelow, the impinging beam will be scattered, rather than reflected from the tube's surface. This unique combination of heat conducting and beam scattering properties renders the present composite material of extreme value in laser beam surgery.

The anisotropic effect may be enhanced through use of a dispersion of oriented particulate graphite. By "a dispersion of oriented particulate graphite" is meant a dispersion of particulate graphite in which the graphite particles are aligned with their a-b planes substantially parallel both to each other and to the major surface of the composite material comprising the particles. Such orientation can be accomplished during fabrication of the composite material. For example, during the extrusion process to form an endotracheal tube, the graphite particles will tend to orient themselves with their a-b planes in the direction of extrusion, or along the longitudinal axis of the tube. Likewise, in forming a sheet by rolling, the particles tend to become oriented with their a-b planes in the direction of the rolling, or parallel to the major surfaces of the sheet. Therefore, when graphite particles are dispersed in a polymer matrix to form a composite material and the particles are oriented with their a-b planes essentially parallel to each other and to the major axis or surface of the composite material, a localized heat buildup in the composite material will be rapidly dissipated by conduction along the major axis of the composite material.

The graphite particles generally constitute from about 5 to 50 weight percent of the composite material. Graphite levels much below 5 weight percent produce little beneficial effect; levels above 50 percent offer no particular advantage while reducing the elasticity and strength of the matrix. Preferably, the graphite is from about 25 to 35 weight percent of the composite material. To provide the desired beam scattering, the graphite particles normally have an average particle size, as measured by standard Coulter counter techniques, of from about 5 to 250 microns. Particles much larger than 250 microns provide little scattering of the impinging beam, while particles much under 5 microns are too difficult to disperse. The preferred particle size will vary depending on the laser beam source, such as YAG, argon, helium-neon and krypton fluoride. When a carbon dioxide laser is employed, the graphite preferably has an average particle size of from about 50 to 100 microns. The relationship between particle size and scattering is well known to those who understand Rayleigh scattering.

The polymer matrix can be of any natural or synthetic, organic or inorganic, nonconducting polymer in which the graphite particles can be dispersed. Such polymers include, for example, thermoplastics such as crude rubber, polyvinyl chlorides, nylons, fluorocarbons, linear polyethylenes, polystyrenes, polypropylenes, and cellulosic and acrylic resins as well as thermosets such as phenolics, alkyds, amino resins, polyesters, epoxides and silicones. The elastomers such as natural rubber (polyisoprene), sodium polysulfide, polychloroprene, butadiene-styrene copolymers, acrylonitrile-butadiene copolymers, ethylene-propylenediene rubbers, isobutylene-isoprene copolymers, polyacrylonitrile, epichlorohydrin, polyurethane, and especially silicone rubber, are preferred in order to provide a composite having a degree of flexibility.

In addition to the graphite particles and polymer matrix, the composite may also include miscellaneous ingredients which do not deleteriously affect its heat conducting and light scattering properties. Such ingredients include, for example, fillers, colorants and softeners.

While the composite material of the present invention may have other shapes, it will normally be in the form of a tube or a sheet. Of particular interest are endotracheal tubes such as that described in U.S. Pat. No. 4,419,095, which is incorporated herein by reference. In preparing the desired tube or sheet, the graphite of selected particle size is normally blended with the selected monomer for the matrix, along with any other miscellaneous ingredient such as colorant, and the monomer is then polymerized and the blend shaped by extrusion or other means, using standard processing techniques. As previously indicated, orientation of the particulate graphite is facilitated during such processing by the forces acting in the flow field.

The following example directed to laser beam surgery is merely illustrative and should not be construed as limiting the invention, the scope of which is defined by the appended claims.

EXAMPLE

A sample of pyrolytic graphite (Pyroid ®, Pfizer Inc., New York, NY) was ground to below 60 mesh (250 microns; U.S. Sieve Series) and compounded at various levels with silicone rubbers of 65 and 80 Shore A hardness. The blends were then press rolled into strips having a thickness of ⅛ inch (3.2 mm).

A 0.75-mm diameter 20 watt carbon dioxide laser beam was directed normal to a major surface of each of the strips to simulate accidental impingement of the laser beam during surgery, using both a single blast of 10-second duration and a series of 5 blasts of 0.5-second duration with momentary pause between blasts. These treatments resulted in the following temperatures on the underside of the strips below the point of impingement:

|  | Silicone Matrix | | | |
| --- | --- | --- | --- | --- |
|  | 65 | | 80 | |
| Temp, °C., at | Exposure, secs. | | | |
| wt % graphite of: | 5 × 0.5 | 10 | 5 × 0.5 | 10 |
| 0 | 48.0* | 120.0* | 44.7* | 91.5* |
| 5 | 40.5 | 86.9 | 39.6 | 78.0 |
| 10 | 41.5 | 88.7 | 36.3 | 72.6 |
| 20 | 37.2 | 75.7 | 35.6 | 66.0 |
| 30 | 36.1 | 72.0 | 35.1 | 63.6 |
| 40 | 35.0 | 72.5 | 33.8 | 52.4 |
| 50 | 35.7 | 62.3 | 34.8 | 57.4 |

*strip penetrated by beam

This testing clearly shows the advantages of the present composite material in laser beam surgery. The unfilled strips, typical of current state-of-the-art endotracheal tubes, were penetrated by the laser beam at both levels of exposure, an intolerable condition since current medical practice requires that the tubes carry highly combustible anaesthetizing gases. In contrast, the present composite, even at graphite levels as low as 5 weight percent, prevented such penetration, with considerable reduction in the inside wall temperature, thus offering greater stability and safety for endotracheal tubes of such composition employed in laser beam surgery.

We claim:

1. A shield for protecting matter from laser beam impingement, the shield being fabricated from a composite comprising a dispersion of particulate graphite in a polymer matrix.

2. The shield of claim 1 wherein the particulate graphite is pyrolytic graphite.

3. The shield of claim 1 wherein the particulate graphite is at least partially oriented in the polymer matrix.

4. The shield of claim 1 wherein the particulate graphite constitutes from about 25 to 35 weight percent of the composite.

5. The shield of claim 1 wherein the particulate graphite has an average particle size of from about 50 to 100 microns.

6. The shield of claim 1 wherein the polymer matrix is silicone rubber.

7. The shield of claim 1 in the form of a sheet or tube.

8. An endotracheal tube fabricated from a composite comprising a dispersion of particulate pyrolytic graphite in an elastomer matrix.

9. A method of reducing the effects from laser beam impingement on a heat-sensitive implement or living tissue, which comprises protecting the implement or tissue with a layer of composite material comprising a dispersion of particulate graphite in a polymer matrix.

10. The method of claim 9 wherein the particulate graphite is pyrolytic graphite and is at least partially oriented in the polymer matrix.

* * * * *